United States Patent [19]

White

[11] 4,263,443

[45] Apr. 21, 1981

[54] CONVERSION OF ALDEHYDES

[75] Inventor: John F. White, Princeton, N.J.

[73] Assignee: Halcon Research and Development Corp., New York, N.Y.

[21] Appl. No.: 963,076

[22] Filed: Nov. 22, 1978

[51] Int. Cl.$^3$ .................... C07C 51/00; C07C 67/00; C07C 69/12

[52] U.S. Cl. ............................ 549/83; 260/346.11; 260/410.9 R; 260/410.9 N; 260/413; 560/1; 560/105; 560/114; 560/231; 560/232; 560/238; 560/240; 562/400; 562/406; 562/496; 562/497; 562/518; 562/519; 562/606; 562/607; 585/357; 585/469; 585/638; 585/733

[58] Field of Search ............... 560/238, 240, 105, 1, 560/232, 231, 114; 562/606, 400, 496, 519, 607, 497, 518, 406; 260/410.9 R, 413, 346.11, 410.9 N; 585/357, 469, 638, 733; 549/83

[56] References Cited

U.S. PATENT DOCUMENTS

| | | | |
|---|---|---|---|
| 3,007,941 | 11/1961 | Copelin et al. | 260/346.11 |
| 3,223,714 | 12/1965 | Manly et al. | 260/346.11 |
| 3,257,417 | 6/1966 | Dunlop et al. | 260/346.11 |
| 3,501,541 | 3/1970 | Dubeck et al. | 585/733 |
| 3,501,546 | 3/1970 | Dubeck et al. | 585/733 |
| 3,639,449 | 2/1972 | Kunugi | 560/238 |
| 3,769,329 | 10/1973 | Paulek et al. | 560/232 |

FOREIGN PATENT DOCUMENTS 45-32402 10/1970 Japan ........................ 585/469

*Primary Examiner*—Jane S. Myers
*Attorney, Agent, or Firm*—William C. Long; David Dick; Riggs T. Stewart

[57] ABSTRACT

Hydrocarbons and esters and/or acids are produced by heating aldehydes in the presence of an alcohol or an alcohol equivalent and in the presence of an iodine or bromine moiety and a rhodium or iridium catalyst.

2 Claims, No Drawings

CONVERSION OF ALDEHYDES

This application relates to the conversion of aldehydes to other compounds and is more particularly concerned with the preparation of hydrocarbons and esters and/or acids from aldehydes and alcohol moieties.

The conversion of aldehydes to other compounds by heating the aldehydes in the presence of various catalysts has heretofore been proposed. For example, Stapp U.S. Pat. No. 3,709,923 discloses the conversion of aldehydes to esters by heating the aldehydes in the presence of boron-containing compound such as boric acid. Pine et al. U.S. Pat. No. 3,287,401 also prepares esters from aldehydes by heating the aldehydes in the presence of a molybdenum catalyst. Another approach to the conversion of aldehydes to esters is shown in Moskovits U.S. Pat. No. 2,918,946 in which an aldehyde and an alcohol are heated in the presence of an esterification catalyst such as sulfuric acid and in the presence of molecular oxygen. Dubeck et al. U.S. Pat. No. 3,501,541 also heats an aldehyde and an alcohol in the presence of a catalyst, in this case a Group VIII metal such as palladium dispersed on titanium dioxide, but the product is a hydrocarbon rather than an ester, the hydrocarbon representing the combination of the hydrocarbyl radical attached to the aldehyde group and the hydrocarbyl radical attached to the hydroxyl group. Hydrocarbons are also produced by the reaction of aldehydes with catalysts. Manly et al. U.S. Pat. No. 3,223,714 shows the conversion of furfural to furan by heating the furfural in the presence of a supported palladium catalyst. Copelin et al. U.S. Pat. No. 3,007,941 and Dunlop et al. U.S. Pat. No. 3,257,417 also convert furan to furfural, the former patent using a palladium catalyst and a basic salt of an alkali metal and the latter patent using a palladium catalyst and calcium acetate.

It is an object of the present invention to provide a novel process for producing hydrocarbons and esters and/or acids.

It is the further object of the invention to provide a process of the character indicated which involves a novel reaction between an aldehyde and an alcohol.

These and other objects are achieved by heating an aldehyde and an alcohol moiety in the presence of a rhodium or iridium catalyst, which is referred to as a Group VIII noble metal catalyst, and in the presence of a halogen moiety. In contrast to the reaction described in patents such as Stapp 3,709,923 wherein the aldehyde is condensed with itself to form an ester containing hydrocarbyl moieties corresponding to the hydrocarbyl moieties of the aldehyde, and in contrast to patents such as Moskovits 2,198,946 wherein the ester has an acid moiety corresponding to the aldehyde and a hydrocarbyl moiety corresponding to the hydrocarbyl moiety of the alcohol, the ester produced in accordance with this invention does not contain the hydrocarbyl moiety of the aldehyde, which is recovered as a hydrocarbon, but contains hydrocarbyl moieties derived solely from the alcohol moiety. The term "alcohol moiety" is used herein to designate an alcohol per se or an alcohol "equivalent" such as an ether, an enol ether, an acetal, a ketal, a hemiacetal, an orthoester or esters of inorganic acids such as borates, phosphates, and the like. The overall reaction which is believed to occur in accordance with the process of the invention may be illustrated by the following equation showing the reaction between an aldehyde and an alcohol.

$$\text{RCHO} + 2 \text{ R'OH} \longrightarrow \text{RH} + \text{R'}-\overset{\overset{\displaystyle O}{\|}}{\text{C}}-\text{OR'} + \text{H}_2\text{O} \qquad (1)$$

The reaction is believed to involve the formation of the carboxylic acid followed by esterification of the acid. The free acid is found in the reaction product along with the ester and the hydrocarbon in some cases.

Thus, in accordance with the invention, an aldehyde and an alcohol moiety are reacted in the presence of the Group VIII noble metal catalyst and in the presence of a halogen moiety which is an iodine or a bromine moiety, e.g., a hydrocarbyl iodide or bromide, under relatively mild conditions of temperature and pressure and are caused to undergo a novel inter-reaction to produce an ester and a compound derived from the aldehyde, i.e., a compound wherein the -CHO group is replaced by hydrogen, e.g., a hydrocarbon.

In carrying out the process of the invention, a wide range of temperatures, e.g., 20° to 350° C., are suitable since the reaction temperature is not critical but temperatures of 100° to 200° C. are preferably employed. Temperatures lower than those mentioned can be used but they tend to lead to reduced reaction rates, and higher temperatures may also be employed but there is no particular advantage in their use. The time of reaction is similarly not a parameter of the process and depends largely upon the temperature employed, but typical residence times, by way of example, will generally fall in the range of 2 to 12 hours. Pressure is also not a parameter of the process, the pressure used merely being one which is appropriate at the temperature employed to maintain the reactants in the desired state. When the reaction is carried out in the liquid phase, the pressure is then merely the pressure required to maintain the liquid phase. In this case, the reaction can be advantageously carried out in an autoclave or similar apparatus. The reaction can, however, also be carried out in the vapor phase and the pressure in that event is selected to give the desired space velocity. Ordinarily, however, pressures are within the range of 20 to 600 psig. At the end of the desired residence time, the reaction mixture is separated into its several constituents, as by distillation, e.g., fractional distillation. In the case of liquid-phase operation, the organic product components can be readily distilled away from the noble metal catalyst.

The process can be carried out in the presence of a solvent or diluent, particularly when the reactant has a relatively low boiling point. The presence of a higher boiling solvent or diluent will make it possible to employ more moderate pressures. The solvent or diluent may be any organic solvent which is inert in the environment of the process. Particularly preferred are hydrocarbons, e.g., octane, benzene, toluene, xylene, ethylbenzene, and the like, ketones such as acetone, methylethyl ketone and the like, carboxylic acids; e.g., acetic acid, propionic acid and the like, and chlorinated aromatic solvents such as chlorobenzene. A solvent or diluent is suitably selected which has a boiling point sufficiently different from the desired product in the reaction mixture so that it can be readily separated, as will be apparent to persons skilled in the art. Water can also be employed as the solvent but when water is used, the products are generally the hydrocarbon and the free acid corresponding to the ester.

The aldehydes suitable for use have the formula RCHO. No critical limitation in the size of the organic group R bonded to the aldehyde radical-CHO is known. Preferably R has up to about fourteen carbon atoms. Like the alcohols, the aldehydes used in this process can contain non-hydrocarbon functional groups. Thus, the aldehydes can have halogen, alkoxy, and similar radicals. Preferably, the organic group attached to the aldehyde radical is composed solely of carbon and hydrogen and it may be saturated or contain one or more double bonds.

The organic group can be selected from many types of radicals. Preferably, it is selected from alkyl, alkenyl, cycloalkyl, aralkyl, aralkenyl, aryl and heterocyclic radicals containing O or S. Typical aldehydes containing alkyl, alkenyl and cycloalkyl radicals include acetaldehyde, propionaldehyde, caprylaldehyde, decylaldehyde, tetradecylaldehyde, acrolein, methacrolein, crotonaldehyde, cyclohexylaldehyde, 2-methylcyclohexylaldehyde, 3-heptylcyclohexylaldehyde, 2,4-diisobutylcyclohexylaldehyde, cyclohexylacetaldehyde, 1,2,3,6-tetrahydrobenzaldehyde, and the like.

Preferred are aldehydes containing an aryl radical in the organic group (especially a phenyl radical) which may be directly connected to the aldehyde radical or may be connected via an ethylenic or alkyl group, such as benzaldehyde and related compounds wherein the aromatic ring is substituted, and phenylacetaldehyde, homologs and analogs thereof, and aryl-substituted alkanols and alkenals. As with all aldehydes used in this invention, it is preferred that the compounds contain up to 14 carbon atoms. Non-limiting examples include benzaldehyde, o,m, or p-tolualdehyde, 2,4-dimethylbenzaldehyde and the position isomers thereof, 2,2,4-trimethyl benzaldehyde and the position isomers thereof, 2,3,4,5-tetramethylbenzaldehyde and the position isomers thereof, pentamethylbenzaldehyde, 4-n-heptylbenzaldehyde, its branched isomers, and the position isomers thereof, phenylacetaldehyde, 3-phenylpropionaldehyde, 4-phenylbutyraldehyde, 5-phenylvaleraldehyde, 8-phenyloctaldehyde, cinnamaldehyde, and the like.

In addition to the above compounds, related species wherein the aromatic nucleus is substituted by a plurality of other alkyl radicals, either alike or different, can be employed.

It is not necessary that the group between the aromatic ring and the aldehyde group be a straight chain. Aldehydes wherein the intermediate group is branched are also applicable. Likewise, the aromatic group need not be attached to a terminal carbon. Thus, compounds such as 5-phenyl-3,4-dimethylvaleraldehyde and 3-phenylbutyraldehyde, and the like, can be employed. Moreover, there may be more than one benzenoid nucleus in the aryl group, i.e., it may be a naphthyl group or the like as illustrated by the above phenyl-containing compounds wherein the phenyl group is substituted by a naphthyl group or a biphenyl group or a diphenyl alkyl group such as a diphenylmethane group, and the like.

Furthermore, as previously mentioned, the R organic group may be cyclic and contain one or more double bonds and may contain heteroatoms, e.g., a cyclohexenyl radical, a propenyl radical, an ethenyl radical, a furyl radical, a thienyl radical, and the like as exemplified by cyclohexene aldehyde, methacrolein, acrolein, furfural and 2-thiophenecarbonal. Thus, for example, when the R is ethenyl, (as in acrolein), the hydrocarbon product will be ethylene. When R is propenyl, the hydrocarbon product will be propylene. The products of the invention have been referred to above as esters and hydrocarbons. As will be apparent, however, when the R group contains a heteroatom, the resulting product derived from the aldehyde will be a hydrocarbon containing the heteroatom and it is in this sense that the word "hydrocarbon" is used.

The alcohols employed in the process of this invention are primary, secondary or tertiary alcohols, i.e., alcohols of the formula R'OH wherein R' represents a primary, secondary or tertiary organic group or radical, preferably a primary group or radical.

No critical limitation on the size of the organic group R' is known but, for economic reasons, organic groups having a maximum of 18 carbon atoms are generally employed, preferably a maximum of 12 carbon atoms, and most preferably a maximum of 8 carbon atoms. The organic group can be substituted with functional groups which do not interfere with the process. Thus, the organic groups can contain halogen and/or alkoxy radicals, or like non-interfering substituents. However, hydrocarbyl organic groups are preferred. In other words, it is preferred that the organic groups be composed solely of carbon and hydrogen.

No critical requirement regarding the structure of the organic group is known and it may be aliphatic, alicyclic or aromatic. Preferably, the group is aliphatic, more preferably paraffinic. Thus, in a highly preferred embodiment, acyclic primary alkanols are preferred. In such alcohols R' is R"CH$_2$—wherein R" is hydrogen or an acyclic radical, having either a straight or a branched chain containing up to about 18 carbon atoms. Typical alkanols of this type are methanol, ethanol, n-propanol, n-butanol, n-hexanol, n-octanol, n-decanol, n-dodecanol, n-octadecanol, 3-methylheptanol-1, 4-methylheptanol-1, 6-methylheptanol-1, 3,3-dimethylheptanol-1, 5,5-dimethylheptanol-1, 6,6-dimethylheptanol-1, 3-methyl-3-ethylpentanol-1, and the like. Especially preferred is methanol. Typical secondary and tertiary alcohols include isopropanol, tertiary-butanol, tertiary-amyl alcohol, cyclohexanol, 2-decanol, 3-ethyl-3-decanol, menthol, linalool, methyl benzyl alcohol, and the like.

As previously mentioned, the alcohol moiety does not have to be in the form of an alcohol per se such as those described above, but may be an alcohol "equivalent" such as an ether, e.g., dimethyl ether, diethyl ether, methyl ethyl ether, methyl benzyl ether, anisole, tetrahydrofuran, isopropyl ethyl ether, dibutyl ether, allyl phenyl ether, tetrahydropyran, diphenyl ether, and the like; an enol ether, e.g., isopropenyl methyl ether, dihydropyran, butyl vinyl ether, methyl cyclohexenyl ether, phenyl propenyl ether, and the like; an acetal, e.g., acetaldehyde diethyl acetal, acrolein dimethyl acetal, dimethoxymethane, benzaldehyde dimethyl acetal, benzaldehyde dibutyl acetal, 1,3-dioxane, 2-phenyl-1,3-dioxane, benzaldehyde ethylene acetal, and the like; a ketal, e.g., 2,2-dimethoxy propane, dimethoxy cyclohexane, 3,3-dibutoxyhexane, isopropyl ethylene ketal, 2-isopropyl-1,3-dioxane, benzophenone dimethyl ketal, and the like; a hemiacetal, e.g., 1-isopropoxyethanol, benzaldehyde methyl hemiacetal, acrolein monomethyl hemiacetal, and the like; an orthoester, e.g., trimethyl orthoformate, trimethyl orthoacetate, trimethyl orthobenzoate, diethyl phenyl orthobutyrate, methyl ethylene orthoacetate, triethyl orthopropionate, and the like, and an ester of an inorganic ester such as, as previously mentioned, a borate, a phosphate, or the like such as trimethyl borate, trimethyl phosphate and the like.

The Group VIII noble metal catalyst, i.e., rhodium or iridium, can be employed in any convenient form, viz., in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly, complexes of the metals can be employed, for example the metal carbonyls, such as iridium carbonyls and rhodium carbonyls, e.g., hexarhodium hexadecacarbonyl, or as other complexes such as the carbonyl halides, e.g., iridium tricarbonyl chloride $(Ir(CO)_3Cl)_2$ or chlorodicarbonyl rhodium dimer, or the acetylacetonates, e.g., rhodium acetylacetonate $Rh(C_5H_7O_2)_3$. Other suitable forms of the Group VIII noble metal include trichlorotrispyridinerhodium(III), tris(triphenylphosphine)hydridorhodiumcarbonyl, dirhodium octacarbonyl, chlorotris(triphenylphosphine)rhodium, bis(triphenylphosphine)chlororhodium carbonyl, and the like. Rhodium is the preferred Group VIII noble metal. The invention also contemplates the use of mixtures of rhodium or iridium catalysts with other Group VIII noble metal catalysts, e.g., mixtures of rhodium and palladium catalysts, and the like. It will be understood that the foregoing compounds and complexes are merely illustrative of suitable forms of the Group VIII noble metal catalyst and are not intended to be limiting in any way.

The halide moiety is an iodide or a bromide, most preferably an iodide, and can be added to the reaction system in any convenient form. For example, the halide is preferably a hydrocarbyl halide, especially a lower alkyl halide such as methyl halide. The halide, however, can be in the form of a metal halide or other halide, such as lithium iodide, magnesium iodide, manganese iodide cadmium iodide, zinc iodide, chromium iodide, lead iodide, cobalt iodide, rubidium iodide, hafnium iodide, iron iodide and the like, and the corresponding bromine compounds. Moreover, the halide may be an organic halide other than a hydrocarbyl halide such as a phosphonium halide, e.g., tetrabutylphosphonium bromide, or an ammonium, or arsonium halide. In addition, the halide can be formed in situ by the complexation of an alkyl halide with a phosphine, e.g., methyl iodide and tributyl phosphine.

It has been found that promoters may be used with the noble metal catalyst and the halide moiety, and a second halide moiety such as dibromoethane is a highly effective promoter particularly when used in combination with a hydrocarbyl halide such as methyl iodide. Particularly good results are obtained with a combination of methyl iodide and dibromoethane. These promoters apparently are effective to maintain the activity of the catalyst. In general, suitable promoters are organic oxidizing agents such as dibromoethane, dibromopropane, N-bromosuccinamide and protonic acids, particularly those stable at 180° C., such as phosphoric acid, trifluoro acetic acid, boric acid, sulfuric acid, and aryl sulfonic acids such as benzene sulfonic acid. The inorganic esters which are effective as alcohol equivalents, e.g., trimethyl borate and trimethyl phosphate, and the like, also have been found to function as promoters. The promoters have been found to be particularly effective when an alcohol is used as a reactant.

The alcohol moiety and the aldehyde are theoretically employed in a 1:1 molar ratio. In practice, however, an excess of either reactant can be employed and the excess can be substantial if desired, e.g., up to 100 mols of one reactant per mol of the other. In general, however, 1.2 to 10 mols of one reactant per mol of the other reactant is suitably employed. In most cases, the alcohol moiety is in excess. In one embodiment of the invention, the aldehyde and the alcohol can be prereacted to form an acetal which can then undergo the reaction with the catalyst and the halogen moiety. This reaction can be illustrated by the following equations:

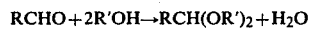

$$RCHO + 2R'OH \rightarrow RCH(OR')_2 + H_2O$$

$$RCH(OR')_2 \rightarrow RH + R'COOR'$$

The amount of Group VIII noble metal catalyst is in no way critical and is not a parameter of the process of the invention and can vary over a wide range. As is well known to persons skilled in the art, the amount of catalyst used is that which will provide a suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 20 to 100,000 mols of aldehyde, preferably 1 mol per 50 to 50,000 mols of aldehyde, and most preferably 1 mol per 100 to 10,000 mols of aldehyde.

When a promoter is used, it can be present in an amount which can vary over a wide range, e.g., 1 to 25 mols per mol of catalyst.

The amount of halogen moiety can vary considerably but it is desirable to employ at least 4 mols per mol of aldehyde, preferably at least 10 mols and, in general, the amount of halogen moiety will range from 6 to 50 mols per mol of aldehyde.

It will be apparent that the above-described reaction lends itself readily to continuous operation in which the reactants and catalyst are continuously supplied to the appropriate reaction zone and the reaction mixture continuously distilled to separate the volatile organic constituents and, in the case of liquid-phase reaction, to provide a residual Group VIII noble metal-containing fraction which can be recycled. In the case of such continuous operation, it will be apparent that the halogen moiety remains in the system at all times subject only to occasional handling losses or purges. The small amount of halogen makeup which may be needed from time to time is preferably effected by supplying the halogen in the form of the hydrocarbyl halide but, as pointed out above, the halogen moiety may also be supplied as another organic halide or as the hydrogen halide or as other inorganic halide, e.g., metal salts.

As previously indicated, the reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, the catalyst and any promoter used, i.e., the catalyst components, may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst, or the catalyst and promoter, followed by drying. Catalyst component concentrations upon the carrier may vary widely, e.g., 0.01 weight percent to 10 weight percent, or higher. Any organic promoter can be either fed with the reactants or complexed with the catalyst. Typical operating conditions for vapor-phase operation are a temperature of 50° to 400° C., preferably 80° to 350° C., and most preferably 150° to 300° C., a pressure of 20 to 500 psig, preferably 40 to 200 psig with space velocities of 100 to 10,000 hr.−1, preferably 200 to 1,000 hr.−1 (STP).

The following examples will serve to provide a full understanding of the invention, but it is to be understood that these examples are given for illustrative purposes only and are not to be interpreted as being limitative of the invention. In Examples 1-5 below, the specified reactants and other components of the charge are added to a 100 ml, glass-lined, stainless-steel Parr bomb, the bomb is sealed and immersed in an oil bath maintained at 160°-200° C. and the contents of the bomb are heated for 2-8 hours. When dimethyl ether is the reactant providing the alcohol moiety, the bomb is first placed in a dry ice/acetone bath to cool it and the dimethyl ether is then added directly from a storage tank. The amount of dimethyl ether charged is determined by weighing the bomb before and after the addition. At the end of the reaction period, the contents of each bomb are poured into a screw-cap bottle and a toluene internal standard (about 3.8 mmol) is added. The reaction product mixture is then subjected to analysis by gas chromatography (G.C.).

EXAMPLE 1

The reactants are 20 ml. of benzaldehyde and 10 ml of methanol in the presence of 0.5 mmol of rhodium chloride trihydrate ($RhCl_3.3H_2O$) as catalyst and 4 mmol of iodine moiety in the form of methyl iodide tributyl phosphine complex. The mixture is heated at 160° C. for 5 hours. G.C. analysis shows the reaction product to comprise 5.1 mmol methyl acetate and 7.1 mmol of benzene.

EXAMPLE 2

Example 1 is repeated except that a temperature of 180° C. and the reaction time of 2 hours are employed. The product contains 2.6 mmol methyl acetate and 3.1 mmol benzene. When the reaction is carried out for 4 hours, the amount of methyl acetate is increased to 10.8 mmol and the amount of benzene is increased to 13.1 mmol. When the reaction is carried out for 8 hours, the amount of methyl acetate is increased to 21.8 mmol and the amount of benzene is increased to 27.7 mmol.

EXAMPLE 3

Example 1 is repeated except that 15 ml of benzaldehyde and 15 ml of methanol are charged and the reaction is carried out at 200° C. for 2 hours. The reaction product contains 7.2 mmol of methyl acetate and 10.2 mmol of benzene. When the reaction is carried out for 4 hours, the amount of methyl acetate is increased to 17.1 mmol and the amount of benzene is increased to 23.6 mmol. When the reaction is carried out for 8 hours, the amount of methyl acetate is increased to 24.7 mmol and the amount of benzene is increased to 31.3 mmol.

EXAMPLE 4

Example 3 is repeated except that the temperature is reduced to 160° C. and the reaction is carried out for 5 hours. The amount of methyl acetate is 2.7 mmol and the amount of benzene is 2.6 mmol.

EXAMPLE 5

Example 4 is repeated except that there is added 0.65 mmol of chromic acetate as a promoter. The reaction product is found to contain 4.8 mmol methyl acetate and 5.1 mmol benzene.

In the following examples, the procedure and equipment described above for examples 1-5 is employed but all runs are made at 180° C. for 8 hours, unless otherwise indicated.

EXAMPLE 6

The reactants are 15 ml of benzaldehyde and 15 ml of methanol in the presence of 0.5 mmol of rhodium chloride trihydrate as catalyst and 2 mmol of iodine moiety in the form of cadmium iodide, G.C. analysis shows the reaction product to comprise 12.4 mmol methyl acetate, 20.1 mmol benzene and 2 mmol acetic acid.

EXAMPLE 7

Example 6 is repeated except that the iodine moiety is in the form of 2 mmol of magnesium iodide. G.C. analysis of the reaction product shows it to contain 9.5 mmol of methyl acetate, 4.9 mmol of benzene and 3.6 mmol of acetic acid.

EXAMPLE 8

Example 6 is again repeated except that the iodine moiety is in the form of 4.0 mmol of lithium iodide. G.C. analysis of the reaction product shows it to contain 7.2 mmol of methyl acetate, 8 mmol of benzene and a trace of acetic acid.

EXAMPLE 9

Example 6 is repeated except that a bromine moiety is used in the form of 8 mmol of tetrabutylphosphonium bromide. G.C. analysis of the reaction product shows it to contain 2.4 mmol of methyl acetate, 3.9 mmol of benzene and a trace of acetic acid.

EXAMPLE 10

Example 9 is repeated except that 2 mmol of 85% phosphoric acid is added as a promoter. G.C. analysis of the reaction product shows it to contain 3.6 mmol of methyl acetate and 5.6 mmol of benzene.

EXAMPLE 11

Example 6 is again repeated except that the iodine moiety is in the form of 4 mmol of tributylmethylphosphonium iodide and 10 ml of acetone is added as a solvent. G.C. analysis of the reaction product shows it to contain 10.1 mmol of methyl acetate and 10.8 mmol of benzene.

EXAMPLE 12

Example 11 is repeated except that 2 mmol 85% phosphoric acid is added as a promoter. G.C. analysis of the reaction product shows it to contain 27.1 mmol of methyl acetate and 29.4 mmol of benzene.

EXAMPLE 13

Example 11 is again repeated except that 17.6 mmol of trimethyl borate is added as a promoter. G.C. analysis of the reaction product shows it to contain 19 mmol of methyl acetate and 19.2 mmol of benzene.

EXAMPLE 14

Example 6 is repeated except that the iodine moiety is in the form of 1 mmol of cadmium iodine and 2 mmol of tributylphosphine methyl iodide complex. G.C. analysis of the reaction product shows it to contain 20.1 mmol of methyl acetate and 21 mmol of benzene.

EXAMPLE 15

Example 14 is repeated except that the iodine moiety is in the form of 2 mmol of cadmium iodide and 4 mmol of tributylmethylphosphonium iodide. G.C. analysis of the reaction product shows it to contain 19.9 mmol of methyl acetate and 21.7 mmol of benzene.

EXAMPLE 16

Example 6 is repeated except that the iodine moiety is in the form of 2 mmol of lead diodide. G.C. analysis of the reaction product shows it to contain 6.6 mmol of methyl acetate, 15.5 mmol of benzene and 13.9 mmol of acetic acid.

EXAMPLE 17

Example 6 is repeated except that the iodine moiety is in the form of 1.3 mmol of chromic iodide. G.C. analysis of the reaction product shows it to contain 5.1 mmol of methyl acetate and 4 mmol of benzene and 13 mmol of acetic acid.

EXAMPLE 18

Example 6 is again repeated except that the iodine moiety is in the form of 4 mmol of tributyl phosphine methyl iodide complex. G.C. analysis of the reaction product shows it to contain 27.8 mmol of methyl acetate and 31.1 mmol of benzene.

EXAMPLE 19

Example 6 is repeated except that the iodine moiety is in the form of 4 mmol tributyl phosphine methyl iodide complex and 10 ml of benzaldehyde and 30 ml of methanol are used. G.C. analysis of the reaction product shows it to contain 15.8 mmol of methyl acetate and 15.6 mmol of benzene.

EXAMPLE 20

Example 19 is repeated except that 2 mmol of 85% phosphoric acid is added as a promoter. G.C. analysis of the reaction product shows it to contain 21 mmol of methyl acetate and 21 mmol of benzene. When the amount of promoter is increased to 4 mmol there are produced 22.6 mmol of methylacetate and 24.3 mmol of benzene. When the amount of promoter is reduced to 1.2 mmol there are produced 41.4 mmol of methyl acetate and 44.7 mmol of benzene.

EXAMPLE 21

Example 19 is repeated except that 4 mmol of trimethyl borate added as a promoter. G.C. analysis of the reaction product shows it to contain 32.6 mmol of methyl acetate and 31.7 mmol of benzene.

EXAMPLE 22

Example 19 is repeated except that 44 mmol of trimethyl borate is added as a promoter. G.C. analysis of the reaction product shows it to contain 33.6 mmol methyl acetate and 29.3 mmol of benzene.

EXAMPLE 23

Example 6 is repeated except that 25.5 g of dimethyl ether are used instead of methanol and the halogen moiety is in the form of 8 mmol of tetrabutylphosphonium bromide. G.C. analysis of the reaction product shows it to contain 6 mmol of methyl acetate and 7.1 mmol of benzene.

EXAMPLE 24

Example 6 is repeated except that 12 g of dimethyl ether are used instead of methanol and the iodine moiety is in the form of 4 mmol of tributyl phosphine methyl iodide complex and the reaction is carried out for four hours. G.C. analysis of the reaction product shows it to contain 9 mmol of methyl acetate, 14.3 mmol of benzene and 4.1 mmol of acetic acid.

COMPARATIVE EXAMPLE

A similar experiment to Example 1 is run except no promoter is added to the rhodium chloride catalyst. The reactants are 15 ml of benzaldehyde and 15 ml of methanol. The 0.5 mmol of rhodium chloride hydrate catalyst contains no iodide promoter. After 8 hours at 180° C., G.C. analysis of the product showed 2.5 mmol of benzene resulting from some decarbonylation of the benzaldehyde, but no methyl acetate or acetic acid.

EXAMPLE 25

The reactants are 15 ml of cinnamaldehyde and 22 g. of dimethyl ether in the presence of 0.5 mmol of rhodium chloride trihydrate as catalyst and 4 mmol of tributylmethylphosphonium iodide and 2 mmol of 85% phosphoric acid. The mixture is heated at 180° C. for 8 hours. G.C. analysis shows 3.6 mmol methyl acetate, 17.5 mmol styrene and 7.7 mmol acetic acid to be present in the product mixture.

EXAMPLE 26

The reactants are 15 ml of 1,2,3,6-tetrahydrobenzaldehyde and 21 g. of dimethyl ether. The catalyst, promoters and reaction conditions are identical to those in Example 25. G.C. analysis shows the product contained 6.5 mmol of methyl acetate and 26.7 mmol of cyclohexene.

EXAMPLE 27

The reactants are 17 ml of benzaldehyde and 3 ml of benzaldehyde dimethyl acetal. The catalyst is 0.5 mmol of rhodium chloride trihydrate and the promoter is 4 mmol of tributylmethylphosphonium iodide. After heating for 8 hours at 180° C., 26.5 mmol of benzene and 21.4 mmol of methyl acetate are detected by G.C. analysis in the product.

EXAMPLE 28

This run is carried out as described in Example 27, except that instead of adding benzaldehyde and its acetal just 20 ml of the benzaldehyde dimethyl acetal is employed. The product is shown by G.C. analysis to contain 3.4 mmol of benzene and 4.6 mmol of methyl acetate. This illustrates that the alcohol and the aldehyde can be pre-reacted prior to reaction in the presence of the Group VIII metal and the iodine moiety.

EXAMPLES 29 and 30

Two runs are made in a glass-lined 1-liter stirred autoclave at 180° C. Both contain 250 ml of benzaldehyde 150 ml of methanol and 10 ml of toluene internal standard at the beginning.

In Example 30, 10 mmol of 1,2-dibromoethane are also added. Samples are taken at timed intervals throughout the runs.

|  | EXAMPLE 29 | | EXAMPLE 30 | |
| --- | --- | --- | --- | --- |
| Hrs | mmol $C_6H_6$ | mmol MeOAc | mmol $C_6H_6$ | mmol MeOAc |
| 2 | 68.0 | 60.7 | 49.8 | 41.8 |
| 4 | 85.1 | 73.7 | 114.7 | 130.9 |
| 6 | 121.2 | 141.9 | 160.2 | 140.9 |
| 8 | 172.1 | 190.2 | 216.4 | 242.4 |
| 12 | 221.8 | 252.9 | 331.1 | 357.9 |

EXAMPLE 31

The reactants are 20 ml of benzaldehyde and 10 ml of methanol in the presence of 0.5 mmol of iridium chloride trihydrate ($RhCl_3.3H_2O$) as catalyst and 4 mmol of iodine moiety in the form of methyl iodide tributylphosphine complex. G.C. analysis shows both methyl acetate and benzene are present in the product solution after heating at 180° C. for 8 hours.

EXAMPLE 32

The reactants are 15 ml of benzaldehyde and 15 ml of trimethylphosphate in the presence of 0.5 mmol of rhodium chloride trihydrate and 4 mmol of tributylmethylphosphonium iodide. The reaction is run at 180° C. for 8 hours. G.C. analysis shows 14.6 mmol of methyl acetate and 12.5 mmol of benzene.

EXAMPLE 33

The reactants are 15 ml of benzaldehyde and 15 ml of diethylether in the presence of 0.5 mmol of rhodium chloride trihydrate and 4 mmol of tributylmethylphosphonium iodide. After heating at 180° C. for 4 hours, G.C. analysis shows 7.1 mmol benzene, 4.5 mmol of ethyl propionate and 2.6 mmol of propionic acid.

EXAMPLE 34

The reactants are 15 ml of benzaldehyde and 15 ml of isopropanol in the presence of 0.5 mmol of rhodium chloride trihydrate and 4 mmol of tributylmethylphosphonium iodide. After heating at 180° C. for 8 hours, both benzene and isobutyric acid and its isopropyl ester are detected in the product solution by G.C. analysis.

EXAMPLE 35

The reactants, 15 ml of benzaldehyde and 23 g of dimethylether, are heated at 180° C. for 8 hours in the presence of 1 mmol of palladium(II) chloride, 0.1 mmol rhodium chloride trihydrate and 6 mmol of tributylmethylphosphonium iodide. G.C. analysis shows 3.2 mmol of methyl acetate and 3.7 mmol of benzene.

What is claimed is:

1. A process which comprises heating an aldehyde and an alcohol moiety, in the presence of a rhodium or iridium catalyst and in the presence of an iodide or a bromide, water being an optional solvent, to produce a product which comprises (a) a compound of the formula RH and an ester, (b) a compound of the formula RH and an ester and an acid, or (c) a compound of the formula RH and an acid, the acid of (c) being obtained when water is used as a solvent, said aldehyde having the formula RCHO and said alcohol having the formula $R^1OH$, $R^1$ being an aliphatic, alicyclic or aromatic hydrocarbon group, optionally containing non-interfering substituents, and $R^1$ being alkyl, alkenyl, cycloalkyl, aralkyl, aralkenyl, aryl, furyl or thienyl.

2. A process as defined in claim 1 further including a promoter for the rhodium or iridium catalyst, the promoter being dibromoethane, dibromopropane, N-bromosuccinamide, a protonic acid stable at 180° C., trimethyl borate or trimethyl phosphate.

* * * * *